(12) United States Patent
Ogaito et al.

(10) Patent No.: US 11,078,412 B2
(45) Date of Patent: Aug. 3, 2021

(54) POLYAMINE AND TYRAMINE ANALYSIS METHOD USING PYRENE CONTAINING FLUORESCENCE DERIVATIZATION REAGENT AND EXCIMER FLUORESCENCE

(71) Applicants: Shimadzu Corporation, Kyoto (JP); Shizuoka Prefecture Public University Corporation, Shizuoka (JP)

(72) Inventors: Makoto Ogaito, Kyoto (JP); Azusa Uchida, Kanagawa (JP); Kenichiro Todoroki, Shizuoka (JP); Tatsuki Nakano, Tokyo (JP); Toshimasa Toyo'Oka, Shizuoka (JP)

(73) Assignees: Shimadzu Corporation, Kyoto (JP); Shizuoka Prefecture Public University Corporation, Shizuoka (JP)

( * ) Notice: Subject to any disclaimer, the term of this patent is extended or adjusted under 35 U.S.C. 154(b) by 278 days.

(21) Appl. No.: 15/555,866

(22) PCT Filed: Mar. 4, 2015

(86) PCT No.: PCT/JP2015/056416
§ 371 (c)(1),
(2) Date: Sep. 5, 2017

(87) PCT Pub. No.: WO2016/139786
PCT Pub. Date: Sep. 9, 2016

(65) Prior Publication Data
US 2018/0051205 A1     Feb. 22, 2018

(51) Int. Cl.
*G01N 21/64* (2006.01)
*G01N 31/00* (2006.01)
(Continued)

(52) U.S. Cl.
CPC .......... *C09K 11/06* (2013.01); *C07D 251/12* (2013.01); *C07D 251/26* (2013.01); *C09K 11/61* (2013.01);
(Continued)

(58) Field of Classification Search
CPC ........ G01N 21/64; G01N 31/00; G01N 33/02; C09K 11/06; C09K 11/61; C07D 251/12
(Continued)

(56) References Cited

U.S. PATENT DOCUMENTS 3,157,651 A * 11/1964 Atkinson ............. C07D 251/16
544/211
3,316,263 A * 4/1967 Ross ..................... C07D 251/38
544/219
(Continued)

FOREIGN PATENT DOCUMENTS

JP      H10-142228 A     5/1998
JP      2001-242174 A    9/2001

OTHER PUBLICATIONS

Winnik, F. M. et al, Macromolecules 1987, 20, 38-44.*
(Continued)

*Primary Examiner* — Arlen Soderquist
(74) *Attorney, Agent, or Firm* — Muir Patent Law, PLLC (57) ABSTRACT

The present invention relates to a method of analyzing a polyamine having a plurality of amino groups in the same molecule or a monoamine having an amino group and a phenolic hydroxyl group in the same molecule on the basis of the measurement result of the intensity of excimer fluorescence emitted as a result of the derivatization of the polyamine or the monoamine with a fluorescence derivatization reagent having a pyrene group. The method is characterized in that the fluorescence derivatization reagent
(Continued)

comprises 2-chloro-4-methoxy-6-(4-(pyren-1-yl) butoxy)-1, 3, 5-triazine represented by the formula (2).

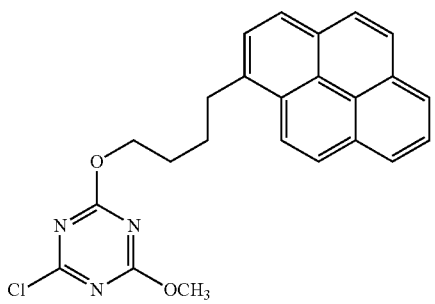

(2)

16 Claims, 7 Drawing Sheets (51) Int. Cl.
G01N 33/02 (2006.01)
C09K 11/06 (2006.01)
C09K 11/61 (2006.01)
C07D 251/12 (2006.01)
C07D 251/26 (2006.01)
G01N 31/22 (2006.01)

(52) U.S. Cl.
CPC .............. G01N 21/64 (2013.01); G01N 31/00 (2013.01); G01N 33/02 (2013.01); C09K 2211/1011 (2013.01); C09K 2211/1018 (2013.01); G01N 31/22 (2013.01)

(58) Field of Classification Search
USPC ............................................. 436/86, 90, 172
See application file for complete search history.

(56) References Cited

U.S. PATENT DOCUMENTS

| | | | | |
|---|---|---|---|---|
| 3,655,662 | A * | 4/1972 | Sietz | C07D 251/26 544/218 |
| 5,922,122 | A * | 7/1999 | Takeda | C09B 57/02 106/413 |
| 2012/0164031 | A1 * | 6/2012 | Serban | C08F 8/24 422/82.08 |
| 2015/0266834 | A1 * | 9/2015 | Nagamori | A61K 31/53 514/241 |

OTHER PUBLICATIONS

Konya, K. G. et al, Chemistry of Materials 1994, 6, 2369-2375.*
Burmeister, J. et al, Tetrahedron Letters 1995, 36, 3667-3668.*
Bruckner, H. et al, Chromatographia Supplement 2003, 57, S-143-S-146.*
Bruckner, H. et al, Journal of Chromatography A 2003, 998, 73-82.*
Hong, J.-H. et al, Bulletin of the Korean Chemical Society 2014, 35, 3158-3162.*
Nakano, T. et al, Analytica Chimica Acta 20015, 880, 145-151.*
Dudley, J. R. et al, Journal of the American Chemical Society 1951, 73, 2986-2990.*
Chin, K.-D. H. et al, Journal of Food Science 1982, 48, 1826-1828.*
Saito, K. et al, Analytical Sciences 1992, 8, 675-680.*
Bruckner, H. et al, Journal of Chromatography 1992, 627, 97-105.*
Rodriguez, I. et al, Journal of Chromatography A 1996, 745, 255-262.*
Krizek, M. et al, Journal of Chromatography A 1998, 815, 243-250.*
Nohta, H. et al, Analytical Chemistry 2000, 72, 4199-4204.*
Paproski, R. E. et al, Journal of Chromatography A, 2002 946, 265-273.*
Molina, M. et al, Electrophoresis 2002, 23, 2333-2340.*
Todoroki, K. et al, Analytical and Bioanalytical Chemistry 2009, 394, 321-327.*
Dai, Q. et al, Analytical Chemistry 2011, 83, 6559-6564.*
Nishikawa, H. et al, Food and Nutrition Sciences 2012, 3, 1020-1026.*
Hayama, T. et al, Analytica Chimica Acta 2012, 755, 93-99.*
Bhushan, R. at al, Chromatographia 2013, 76, 1087-1096.*
Etter, R. et al, Mitteilungen aus dem Gebiete der Lebensmitteluntersuchung und Hygiene 1990, 81, 106-119.*
Yoshida, H. et al, Analytical Sciences 2001, 17, 107-112.*
Nakano, Y. et al, Journal of Chromatography B 2000, 774, 165-172.*
Yoshitake, T. et al, Journal of Neuroscience Methods 2003, 127, 11-17.*
Nakano, Y. et al, Analytical Sciences 2004, 20, 489-493.*
Bhushan, R. et al, Amino Acids 2011, 40, 403-409.*
Hideyuki Yoshida et al., "Simultaneous Determination of Histamine and Histidine by Liquid Chromatography Following Intramolecular Excimer-forming Fluorescence Derivatization with Pyrene-labeling Reagent", Analytical Sciences, Mar. 2004, vol. 20, pp. 557-559.
Heidi S. Marks (Rupp) and Collin R. Anderson, "Determination of putrescine and cadaverine in seafood (finfish and shellfish) by liquid chromatography using pyrene excimer fluorescence", Journal of Chromatography A, 1094 (2005), pp. 60-69.
Hideyuki Yoshida et al., "A simple liquid chromatography method based on intramolecular excimer-forming derivatization and fluorescence detection for the determination of tyrosine and tyramine in urine", Journal of Chromatography B, 821 (2005), pp. 88-93.
Kenichiro Todoroki et al., Journal of Agricultural and Food Chemistry, 2014, 62, pp. 6206-6211.
26W-pm04S, Feb. 2, 2015, non-official translation (Nakano, Tatsuki, 'Development of high-sensitivity/highly selective analysis method for histamines in soy sauce using novel excimer fluorescence derivatization reagent', The Pharmaceutical Society of Japan, 135th Annual Meeting, summary of presentations).

* cited by examiner

50 ppm Him Standard Goods

Confirmation of Derivative by MS

POLYAMINE AND TYRAMINE ANALYSIS METHOD USING PYRENE CONTAINING FLUORESCENCE DERIVATIZATION REAGENT AND EXCIMER FLUORESCENCE

TECHNICAL FIELD

The present invention relates to a fluorescence derivatization reagent used for an analysis of nonvolatile amines such as histamine and tyramine using high-performance liquid chromatography (HPLC), and also relates to an amine analysis method using the fluorescence derivatization reagent.

BACKGROUND ART

Nonvolatile amines such as histamine (Him) and tyramine (Tym) are physiologically active substances produced by decomposition of proteins and amino acids by microorganisms, and it is known that excessive intake of these amines causes allergy-like food poisoning. For this reason, the amount of nonvolatile amines contained in foods is regulated in many countries of the world.

One of foods containing the aforementioned nonvolatile amines is soy sauce which is a Japanese traditional fermented food (seasoning). Since soy sauce is produced by fermenting soybeans and wheats with microorganisms such as lactic acid bacteria and yeast, histamine and tyramine derived from soybean protein are produced in the production process. Therefore, it is important to grasp the amount of histamine and tyramine contained in soy sauce in terms of quality control. There is a demand for a method of conveniently and highly sensitively measuring the amount of nonvolatile amine in the production process of soy sauce.

As an analysis method of nonvolatile amines in foods, a dansyl fluorescence derivatization-HPLC analysis method shown in the Food Hygiene Inspection Guidelines and an HPLC-tandem mass spectrometry (LC-MS/MS) are common. However, the dansyl fluorescence derivatization-HPLC analysis method requires complicated pretreatment operations, and further has problems of poor sensitivity and selectivity. On the other hand, although the sensitivity and selectivity are excellent, the LC-MS/MS uses an expensive and large-scale apparatus, so it is difficult to implement it at a medium-sized food factory or the like.

PRIOR ART

Patent Document

Patent Document 1: Japanese Unexamined Patent Application Publication No. H10-142228
Patent Document 2: Japanese Unexamined Patent Application Publication No. 2001-242174

Non-Patent Document

Non-Patent Document 1: Hideyuki Yoshida, et al., "Simultaneous Determination of Histamine and Histidine by Liquid Chromatography Following Intramolecular Excimer-forming Fluorescence Derivatization with Pyrene-labeling Reagent", Analytical Sciences, March 2004, Vol. 20, pp. 557-559
Non-Patent Document 2: Heidi S. Marks (Rupp), and Collin R. Anderson, "Determination of putrescine and cadaverine in seafood (finfish and shellfish) be liquid chromatography using pyrene excimer fluorescence", Journal of Chromatography A, 1094(2005), pp. 60-69
Non-Patent Document 3: Hideyuki Yoshida, et al., "A simple liquid chromatography method based on intramolecular excimer-forming derivatization and fluorescence detection for the determination of tyrosine and tyramine in urine", Journal of Chromatography B, 821(2005), pp. 88-93
Non-Patent Document 4: Kenichiro Todoroki, et al., Journal of Agricultural and Food Chemistry, 2014, 62, pp. 6206-6211

SUMMARY OF THE INVENTION

Problems to be Solved by the Invention

In recent years, excimer fluorescence derivatization-HPLC method using a reagent (pyrene reagent) containing a compound having a pyrene group has been developed (see Patent Documents 1 and 2). In this analysis method, a polyamine having two or more amino groups in one molecule is fluorescently derivatized with a pyrene reagent to thereby introduce a plurality of pyrene groups in the polyamine one molecule, a polyamine (i.e., labeled polyamine) having an excited dimer (excited-state dimer, hereinafter referred to as "excimer") formed as a result thereof is separated using HPLC, and the intensity of the fluorescence (excimer fluorescence) is measured. Since the wavelength of excimer fluorescence is different from the fluorescence wavelength emitted from pyrene alone (monomer), even in cases where a monoamine or a pyrene reagent is contained in the separated sample, a polyamine can be selectively analyzed with high sensitivity.

As the pyrene reagent, 4-(1-pyrene) butyric acid chloride and active ester type 4-(1-pyrene) butyric acid N-hydroxysuccinimide and the like are used, but both of them are high in hygroscopicity and are readily hydrolyzed, so they are not suitable for long-term storage. Further, when fluorescently derivatizing a polyamine, a solution in which powdered pyrene reagent is dissolved in a solvent is used. However, conventional pyrene reagents can only be stored for several days in a state of being dissolved in a solvent (see Non-Patent Documents 1 to 3). Therefore, a pyrene reagent had to be prepared every time fluorescently derivatizing a polyamine, so the workability was poor. Furthermore, conventional pyrene reagents had a large difference between reactive lots and there was a problem in analytical reproducibility.

Although the case of analyzing a polyamine using a pyrene reagent was described above, recently, it has been found that a monoamine such as tyramine having an amino group and a phenolic hydroxyl group in one molecule also forms excimer by being fluorescently derivatized with a pyrene reagent. Therefore, similar problems arise also in cases where a monoamine is analyzed using the aforementioned pyrene reagent.

The problems to be solved by the present invention is to provide a highly sensitive and selective amine analysis method and to improve storage stability and analytical reproducibility of a fluorescence derivatization reagent used in the analysis method.

Means for Solving the Problems

A compound to be used as a fluorescence derivatization reagent for an amine is based on a pyrene to which a reactive functional group with an amino group or a phenolic hydroxyl group is bonded. The inventors of the present application have searched for the structure of a reactive functional group which is hardly hydrolyzed in order to improve the storage stability of a fluorescence derivatization reagent. As a result of the search, the inventors found that a pyrene derivative having a reactive functional group such as 2-chloro-4-methoxy-6-substituted-1, 3, 5-triazine or the like is effective.

Specifically, a fluorescence derivatization reagent according to the present invention is characterized in that the fluorescence derivatization reagent includes a new compound represented by the following general formula (1):

(1)

Here, X denotes a halogen element, $R_1$ denotes an alkyl group, and $R_2$ denotes an alkyl chain. In particular, X is preferably Cl (chlorine) excellent in reactivity with an amino group or a phenolic hydroxyl group. If the carbon number in the alkyl group and the alkyl chain is large, it is difficult for a monoamine and a polyamine derivatized with a fluorescence derivatization reagent to be eluted from the HPLC column. Therefore, it is preferable that $R_1$ be an alkyl group having a carbon number of 1 to 4 and $R_2$ be an alkyl chain having a carbon number of 1 to 4. Pyrene alcohol is one of raw material compounds of the compound represented by the general formula (1), but pyrene alkyl alcohols having a carbon number of 1 to 4 in the alkyl chain are commercially available and can be easily obtained. Therefore, also from this viewpoint, the carbon number of the alkyl chain is preferably 1 to 4. Furthermore, the fluorescence derivatization reagent according to the present invention preferably includes a compound (2-chloro-4-methoxy-6-(4-(pyren-1-yl) butoxy)-1, 3, 5-triazine) represented by the following formula (2) in which X is Cl (chlorine), $R_1$ is a methyl group, and $R_2$ is a butyl chain.

(2)

The halogen group of the compound represented by the general formula (1) selectively binds to an amino group or a phenolic hydroxyl group. Therefore, in cases where a target substance is a substance (polyamine) having a plurality of amino groups in the same molecule or a target substance is a substance (monoamine) having an amino group and a phenolic hydroxyl group in the same molecule, the target substance and the compound react with each other to thereby form excimer of a pyrene, and excimer fluorescence is emitted. Therefore, by measuring the intensity of this excimer fluorescence, the target substance can be detected.

A substance having only one amino group in the same molecule or a substance having only one phenolic hydroxyl group in the same molecule also become a substance which reacts with the aforementioned compound and emits fluorescence. Therefore, the fluorescence derivatization reagent according to the present invention can also be used for fluorescence derivatization (labeling) of such a substance. In this case, since the wavelength of the excimer fluorescence (475 nm) and the wavelength of fluorescence emitted from the pyrene alone (375 nm) are different from each other, by measuring the fluorescence intensity of each wavelength, it is possible to detect both of them in a distinctive manner.

Further, the amine analysis method according to the present invention is a method of analyzing a polyamine having a plurality of amino groups in the same molecule and/or a monoamine having an amino group and a phenolic hydroxyl group in the same molecule on a basis of a measurement result of intensity of excimer fluorescence emitted as a result of derivatization of the polyamine and/or the monoamine with a fluorescence derivatization reagent having a pyrene group, and is characterized in that the fluorescence derivatization reagent contains 2-chloro-4-methoxy-6-(4-(pyren-1-yl) butoxy)-1, 3, 5-triazine represented by the following formula (2).

(2)

Effects of the Invention

The fluorescence derivatization reagent according to the present invention selectively binds to an amino group or a phenolic hydroxyl group. Further, when the fluorescence derivatization reagent is bound to a substance having a plurality of amino groups in the same molecule or an amino group and a phenolic hydroxyl group in the same molecule, excimer fluorescence is emitted. Therefore, by measuring the intensity of the excimer fluorescence, the amount of the substance can be selectively and highly sensitively measured. In addition, the fluorescence derivatization reagent according to the present invention is low in hygroscopicity, so it is excellent in storage stability, and even in a state in which it is dissolved in a solvent, reactivity can be maintained for a long period of time as compared with a conventional fluorescence derivatization reagent.

EMBODIMENT FOR CARRYING OUT THE INVENTION

A compound according to the present invention is a compound useful as an excimer fluorescence derivatization reagent represented by the following general formula (1).

(1)

In the general formula (1), X represents a halogen element, $R_1$ represents an alkyl group, $R_2$ represents an alkyl chain. In particular, 2-chloro-4-methoxy-6-(4-(pyren-1-yl)butoxy)-1, 3, 5-triazine (CMPT) represented by the following formula (2) in which X denotes Cl (chlorine), $R_1$ denotes a methyl group, and $R_2$ denotes a butyl chain) is excellent in reactivity with a polyamine and in storage stability.

(2)

Hereinafter, examples of a polyamine analysis method using CMPT will be described. In the following, the case in which a histamine is analyzed will be mainly described, which is also applicable to a polyamine other than a histamine, or a monoamine having an amino group and a phenolic hydroxyl group in the same molecule such as a tyramine.

EXAMPLES (1) Production Method of CMPT

Figure 1:
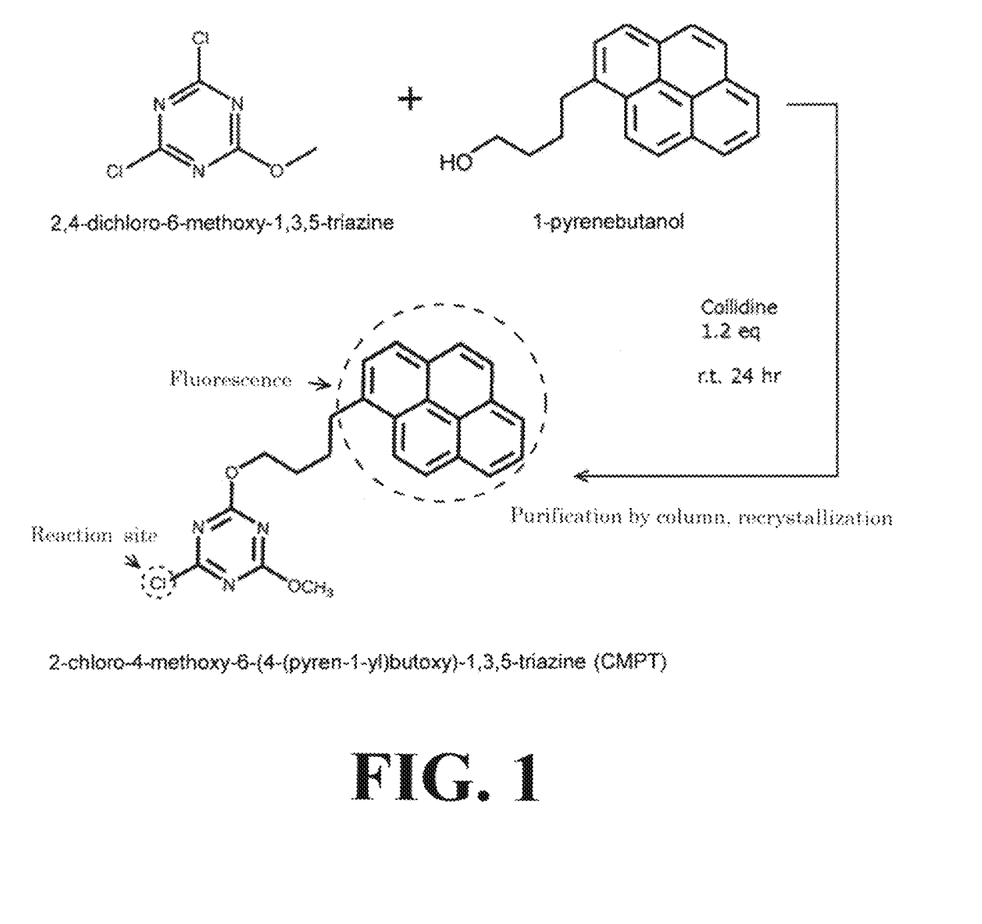
FIG. 1 is a reaction formula of 2, 4-dichloro-6-methoxy-1, 3, 5-triazine and 1-pyrenebutanol showing a synthesis example of CMPT according to one embodiment of the present invention.

As shown in FIG. 1, 1.2 equivalents of Collidine was added to 1 equivalent of 2, 4-dichloro-6-methoxy-1, 3, 5-triazine and 1 equivalent of 1-pyrenebutanol, and the mixture was left at room temperature for 24 hours. This solution was separated by a high performance liquid chromatograph (HPLC apparatus) and then purified by recrystallization. When the obtained product was confirmed by an NMR analysis and a mass spectrometry (MS), it was identified as a compound (CMPT) represented by the following formula.

(2)

In CMPT, the pyrene group is a fluorescence site and the Cl group is a reaction site.

(2) Consideration of Solution for CMPT

To search for bases and solvents suitable for an excimer fluorescence derivatization reaction of a histamine using CMPT, the state of a solution in which CMTP was dissolved in three kinds of bases (potassium carbonate, Collidine, Pyridine) and seven solvents (DMF (N, N-dimethylformamide), DMSO (Dimethyl sulfoxide), THF (tetrahydrofuran), ACN (acetonitrile), ethyl acetate, chloroform, acetone) was observed. The results are shown in Table 1. "x" in Table 1 indicates a combination of a base and a solvent in which CMPT was not completely dissolved.

TABLE 1

| Base/solvent | DMF | DMSO | THF | ACN | Ethyl acetate | Chloroform | Acetone |
|---|---|---|---|---|---|---|---|
| Potassium carbonate | ○ | X | X | X | X | X | X |
| Collidine | ○ | X | X | X | X | X | X |
| Pyridine | ○ | X | X | X | X | X | X |

From Table 1, it is understood that DMF is excellent as a solvent for CMPT. There was no difference in solubility of CMPT in any of potassium carbonate, collidine, and pyridine. However, in a solution using potassium carbonate, precipitation of CMPT was observed when water was added. Considering that water is added by a pretreatment for separating a histamine in soy sauce as described later, it is not preferable to use potassium carbonate. Further, the excimer fluorescence intensity when a histamine was fluorescently derivatized with a solution using a pyridine as a base and a solution using collidine was measured, the intensity of excimer fluorescence was larger in pyridine than in collidine. Therefore, in this example, pyridine was adopted as a base used for the histamine analysis.

Figure 2:
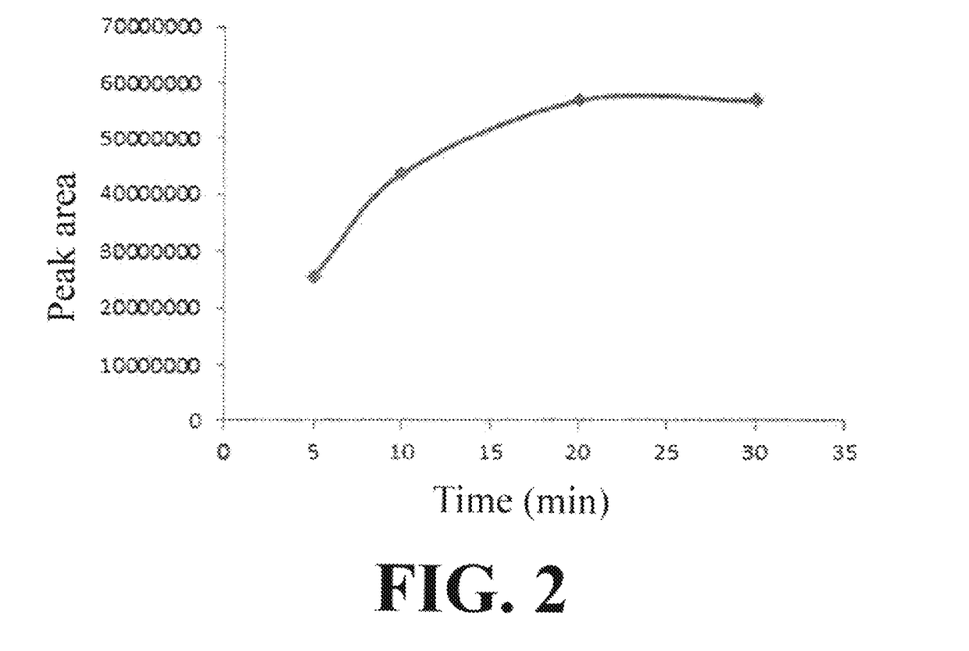
FIG. 2 is a graph showing a relationship between a reaction time and fluorescence intensity when excimer fluorescence intensity was detected after fluoresamine derivatization of a histamine by dissolving a histamine ACN solution in a DMF solution containing pyridine and CMPT.
Figure 3:
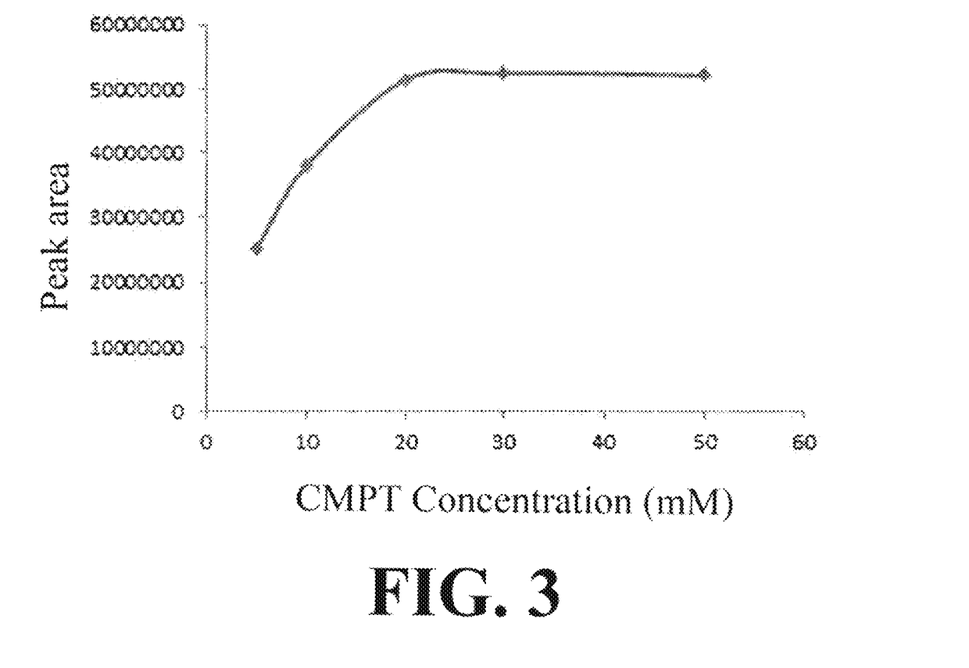
FIG. 3 is a graph showing a relationship between a concentration of CMPT and fluorescence intensity when excimer fluorescence intensity was detected after fluoresamine derivatization of a histamine by dissolving a histamine ACN solution in a DMF solution containing pyridine and CMPT.

(3) Consideration of Reaction Time of Dimerization of Excimer Fluorescence and Concentration of CMPT FIGS. 2 and 3 show the results of detecting the excimer fluorescence intensities by dissolving 10 μL of a histamine ACN solution in 3 μL of pyridine and 20 μL of DMF solution of CMPT and fluorescently derivatizing the histamine and then separating the fluorescence derivatization histamine by HPLC. FIG. 2 shows the relationship between the reaction time and the fluorescence intensity (area) when the concentration of CMPT was set to 20 mM and the reaction temperature was set to 50° C. FIG. 3 shows the relationship between the concentration of CMPT and the fluorescence intensity when the reaction temperature was set to 50° C. and the reaction time was set to 20 minutes. As can be seen from FIG. 2, the fluorescence intensity gradually increased until the reaction time reached 20 minutes, but the fluorescence intensity hardly changed after 20 minutes. As can be seen from FIG. 3, the fluorescence intensity gradually increased in the concentration range up to 20 mM, but the fluorescence intensity hardly changed in the concentration range larger than 20 mM. From the viewpoint of shortening the time required for the histamine analysis and reducing the amount of CMPT used for the histamine analysis, the reaction time for excimer fluorescence derivatization in the histamine analysis according to this example was set to 20 minutes and the CMPT concentration was set to 20 mM.

Figure 4A:
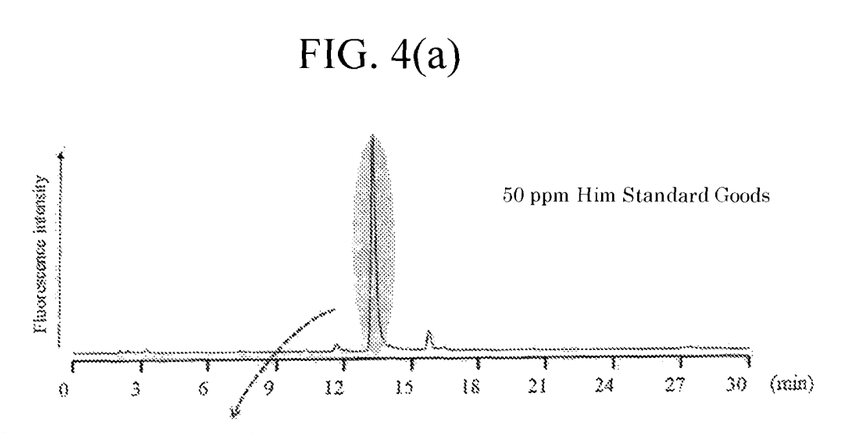
FIGS. 4(a), 4(b) and 4(c) show HPLC analysis results (FIG. 4(a)), HPLC conditions (FIG. 4(c)) and MS results (FIG. 4(b)) when histamine was fluorescently derivatized with CMPT at a CMPT concentration of 20 mM and a reaction time of 20 minutes.
Figure 4B:
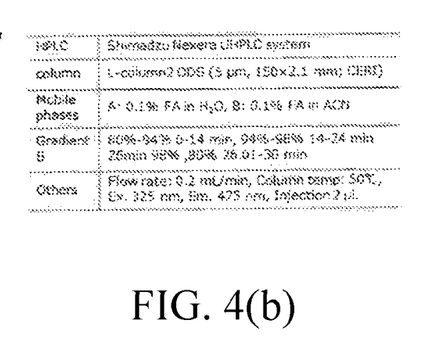
Figure 4C:
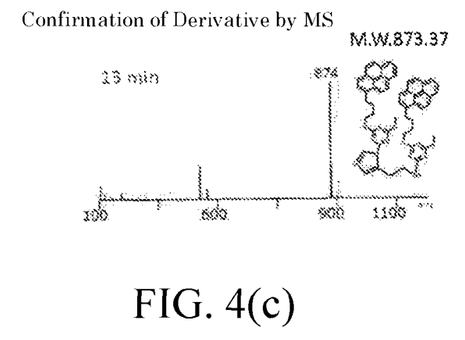

The results of HPLC analysis of the histamine (standard product of 50 ppm) performed under the conditions are shown in FIG. 4(a), and the conditions of HPLC at this time are shown in FIG. 4(b). Further, from FIG. 4(c) showing the results of the MS analysis of substances in which excimer fluorescence was detected by HPLC analysis, it was confirmed that substances in which 2 molecules of CMPT bound to 1 molecule of histamine were generated.

(4) Confirmation of Storage Stability of CMPT in Solution State

Figure 5:
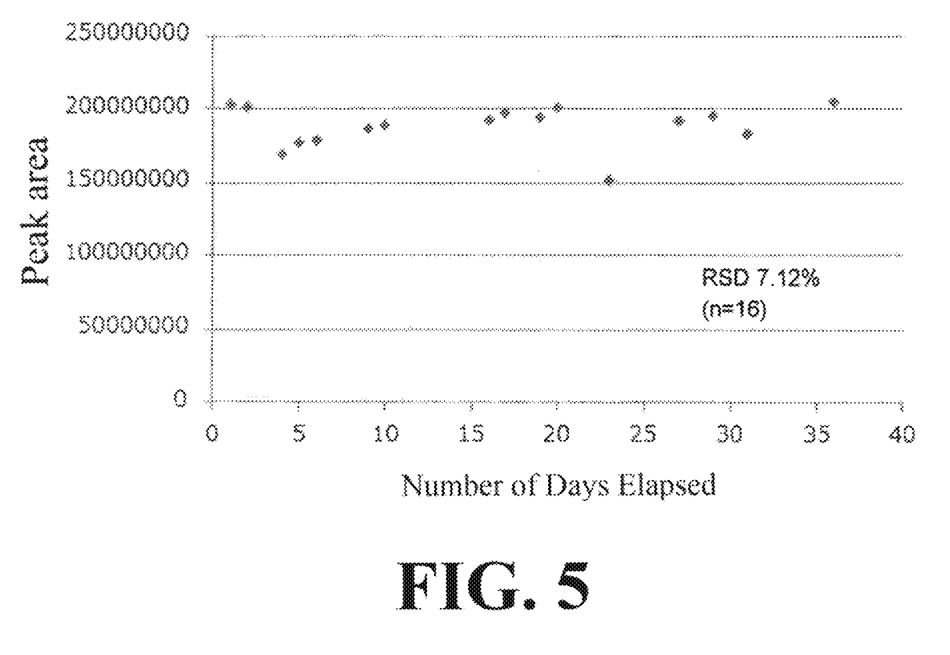
FIG. 5 is a graph showing a relationship between excimer fluorescence intensity and a storage time.

CMPT was dissolved in DMF to prepare a solution. After storing this solution at room temperature, a histamine was fluorescently derivatized with this solution. The resulting fluorescence derivatization histamine was separated using HPLC and the intensity of the excimer fluorescence was obtained. As a result, the relationship between the excimer fluorescence intensity and the storage time became as shown in FIG. 5. As can be seen from FIG. 5, even in the state of a DMF solution, CMPT did not deteriorate in reactivity with a histamine for more than 40 days, and was capable of fluorescently derivatizing. From this, it is understood that CMPT is superior to a conventional excimer fluorescence derivatization reagent in storage stability in a solution state.

(5) Consideration of Pretreatment Conditions

Figure 6A:
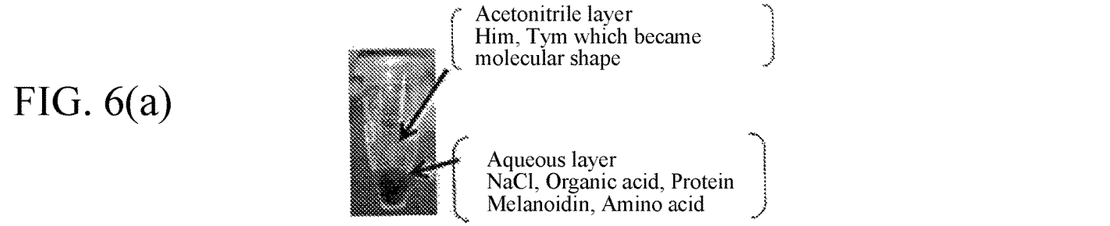
FIG. 6(a) shows an image showing a state in which soy sauce is separated into an aqueous layer and an acetonitrile layer.

When amines contained in soy sauce are analyzed by LC-MS/MS, a pretreatment for separating amines from other components (salt, organic acid, protein, melanoidin, amino acids, etc.) is necessary. As this pretreatment method, the method described in Non-Patent Document 4 is known. In this method, 0.1 M of magnesium sulfate (20 μL), 1M of sodium hydroxide (20 μL, pH 10), and 320 μL of acetonitrile were added to soy sauce (20 μL), and centrifuged to separate an acetonitrile layer containing amines and an aqueous layer containing other components (See FIG. 6(a)). Magnesium sulfate is added to salt out protein, etc., and sodium hydroxide is added to adjust the pH and increase the amount of molecule type histamine. By reference to this pretreatment method, the present inventors considered pretreatment conditions suitable for fluorescently derivatizing a histamine with CMPT.

Figure 6B:
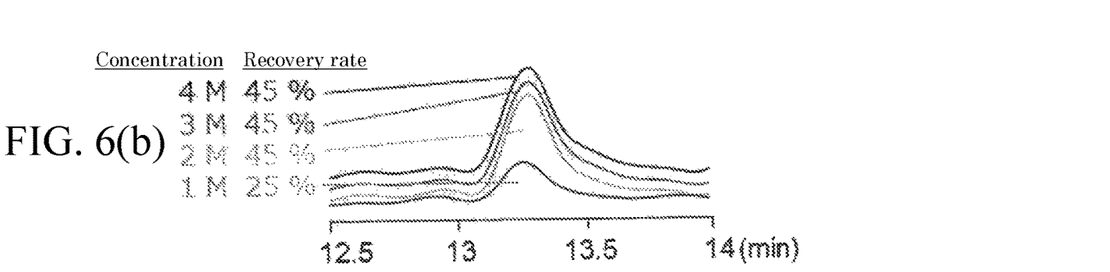
FIG. 6(b) shows a graph showing a relationship between a sodium hydroxide concentration and a recovery rate.
Figure 6C:
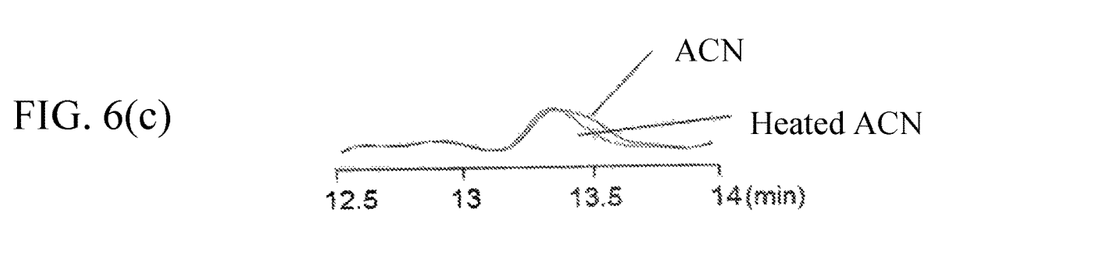
FIG. 6(c) shows a graph showing a difference in recovery rate when using heated ACN and unheated ACN.

Specifically, the proportion (recovery rate (%)) of the histamine recovered in the acetonitrile layer when a sample containing a histamine having a known concentration was separated into an acetonitrile layer and an aqueous layer was investigated for both of a case in which the concentration of the sodium hydroxide was changed to 1 to 4M FIG. 6(b)) and a case in which the unheated acetonitrile and heated acetonitrile were used (FIG. 6(c)).

As can be understood from FIG. 6(b), when the sodium hydroxide concentration was 1M, the recovery rate of the histamine was 25%, but in the range of 2M to 4M, the recovery rate of the histamine was 45%. From the above, it seems that in the sodium hydroxide used for a pretreatment of soy sauce, the suitable concentration range is 2M to 4M.

Further, as can be understood from FIG. 6(c), when the heated ACN was used, the peak shape of the fluorescence derivatization histamine was in a bilaterally symmetrical shape, but when the unheated ACN was used, the peak shape of the fluorescence derivatization histamine was in a bilaterally asymmetrical shape. This is probably because the protein in the sample could not be sufficiently removed when using the unheated ACN and the fluorescence peak of the substance derived from the protein overlapped with the fluoresce peak derived from the histamine. Therefore, it seems preferable to use the heated ACN rather than the unheated ACN for pretreatment of soy sauce.

Figure 7:
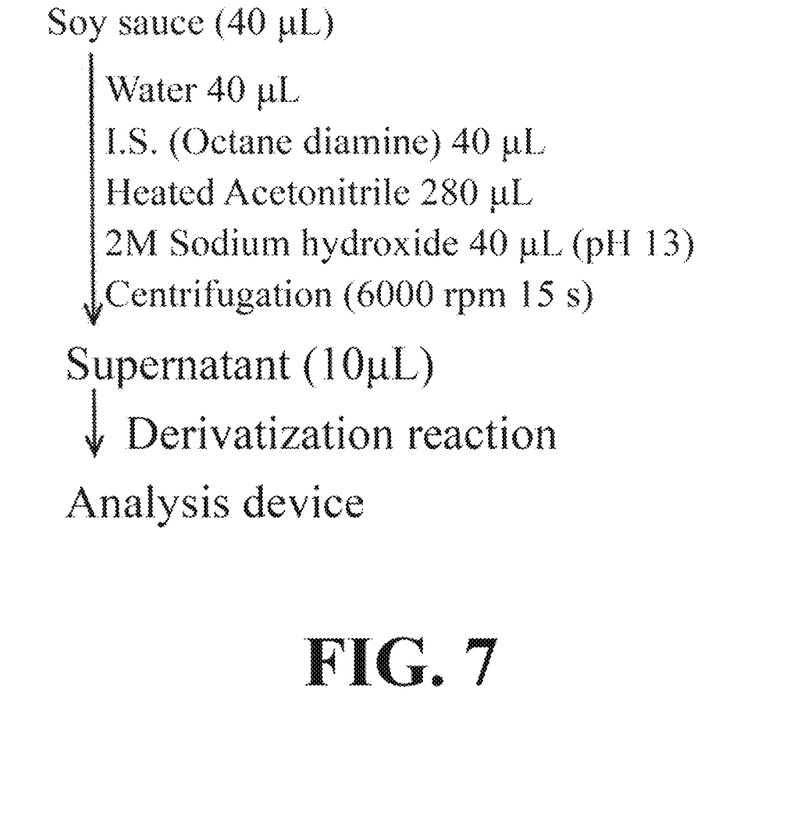
FIG. 7 shows pretreatment conditions of a histamine analysis method according to this example.
Figure 8:
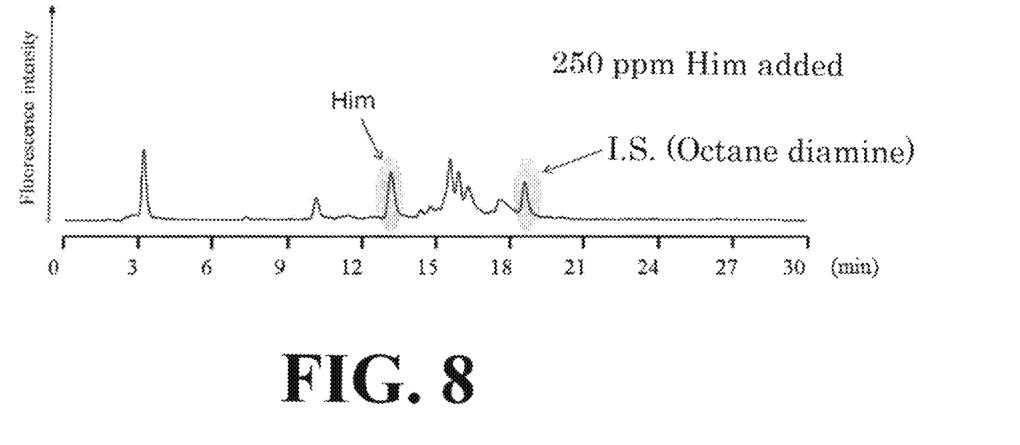
FIG. 8 is a chromatogram showing a result of histamine detection using the histamine analysis method according to this example.
Figure 9:
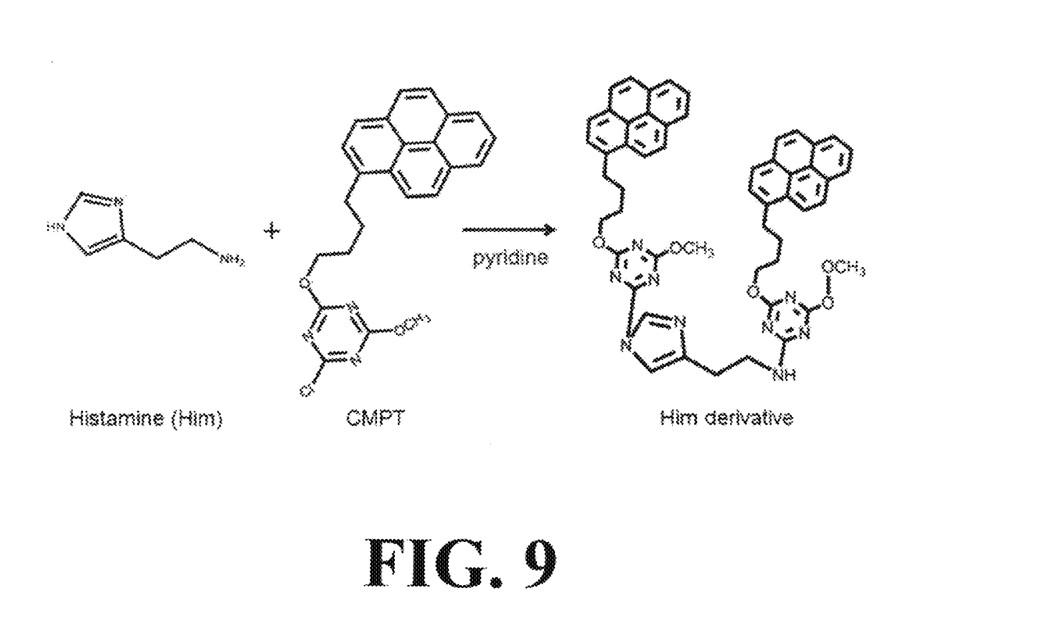
FIG. 9 shows a reaction between histamine and CMPT.

On the basis of the results of the aforementioned (1) to (5), the pretreatment conditions of soy sauce in the histamine analysis according to this example were determined as contents shown in FIG. 7. Here, octanediamine was used as the internal standard (Internal Standard (I.S)). Further, a DMF solution (20 mM) of CMPT was added to the acetonitrile layer separated to the aqueous layer by this pretreatment to fluorescently derivatize the amine (histamine), and thereafter excimer fluorescence intensity detection was detected by the HPLC analysis. The results is shown in FIG. 8. From this result, it was confirmed that histamine was fluorescently derivatized by the reaction shown in FIG. 9 and pyrene excimer was formed. Further, the detection limit (Limit of detection, LOD), the quantitation lower limit (Limit of quantitation, LOQ), linearity, and calibration curve range of the histamine analysis at this time are shown in Table 2. From Table 2, it was found that the histamine analysis according to this example can obtain sufficient linearity and sensitivity for analyzing the histamine in soy sauce.

TABLE 2

| Compound | LOD S/N = 3 (ppm) | LOQ (ppm) | Linearity | Calibration curve range |
|---|---|---|---|---|
| Histamine | 7.5 | 25 | 0.9993 | 25 to 500 |

Next, for a plurality of samples different in histamine concentration, the intra-day variation of the histamine analysis and the inter-day variation of the histamine analysis were examined. The results are shown in Table 3.

TABLE 3

| Addition concentration | | Precision (%) | Accuracy (%) |
|---|---|---|---|
| 25 ppm | Intra-day | 2.05 | 120.7 |
| | Inter-day | 6.01 | 123.5 |
| 50 ppm | Intra-day | 4.85 | 98.0 |
| | Inter-day | — | — |
| 100 ppm | Intra-day | 2.76 | 96.0 |
| | Inter-day | 3.07 | 92.6 |
| 250 ppm | Intra-day | 5.61 | 95.1 |
| | Inter-day | — | — |
| 500 ppm | Intra-day | 3.26 | 96.9 |
| | Inter-day | 5.04 | 93.1 |

Intra-day n = 6,
Inter-day n = 2 × 6 days

As can be seen from Table 3, the intra-day fluctuations were 2.05 to 5.61%, and the inter-day fluctuations was 3.07% to 6.01%. Further, the accuracy (trueness) was 92.6 to 123.5%. From the above, the histamine analysis under the aforementioned pretreatment conditions was found to be excellent both in reproducibility and accuracy.

Next, a quantitative analysis of a histamine was carried out by the histamine analysis method according to this example, using soy sauce of the same type as the soy sauce described in Non-Patent Document 4 as a sample. The results are shown in Table 4. The column at the right end of Table 4 shows the histamine quantification value obtained by the MS analyzer described in Non-Patent Document 4.

TABLE 4

| Sample No. | Type | Manufacturing company | Him quantification value | Him quantification value (Document value) |
|---|---|---|---|---|
| 1 | Dark soy sauce | A | 1.34 | 2.0 |
| 2 | Dark soy sauce | B | 241.0 | 234.5 |
| 3 | Dark soy sauce | C | 11.0 | 14.1 |
| 4 | Dark soy sauce | D | 34.1 | 32.6 |
| 5 | Dark soy sauce | E | 768.05 | 774 |
| 6 | Dark soy sauce | F | 1.45 | 1.2 |
| 7 | Light soy sauce | B | 362.1 | 363.7 |
| 8 | Light soy sauce | G | 1.24 | 1.9 |
| 9 | Light soy sauce | H | 9.91 | 11.1 |
| 10 | Refermented soy sauce | B | 65.7 | 62.5 |
| 11 | Saishikomi (refermented) soy sauce | I | 172.3 | 173 |
| 12 | Saishikomi (refermented) soy sauce | G | 47.0 | 46.2 |
| 13 | Tamari (rich) soy sauce | J | 138.9 | 131.1 |

As can be understood from Table 4, the histamine analysis method according to the present example also yielded the same degree of quantitative value as that of the MS analysis method. From this, it was found that the histamine analysis method according to this example is an effective method of measuring the amount of histamine in soy sauce.

It should be noted that the aforementioned examples are merely examples of the present invention, and even if appropriate modifications and additions are made within the scope of the gist of the present invention, it is encompassed within the claim of the present application.

The invention claimed is:

1. An amine analysis method of analyzing a polyamine having a plurality of amino groups in a same molecule or tyramine, the method comprising:
   preparing a sample containing the polyamine or tyramine;
   adding a fluorescence derivatization reagent having a pyrene group to the sample;
   analyzing the polyamine or tyramine on a basis of a measurement result of intensity of excimer fluorescence emitted as a result of derivatization of the polyamine or tyramine with the fluorescence derivatization reagent,
   wherein the fluorescence derivatization reagent comprises a compound represented by the general formula (1):

(1)

wherein X represents a halogen element, $R_1$ represents an alkyl group, and $R_2$ represents an alkyl chain;
   and wherein the fluorescence derivatization reagent is dissolved in a solvent.

2. The amine analysis method as recited in claim 1, wherein the fluorescence derivatization reagent comprises a 2-chloro-4-methoxy-6-(4-(pyren-1-yl) butoxy)-1, 3, 5-triazine represented by the following general formula (2):

(2)

3. The amine analysis method of claim 1, wherein the amine is in food fermented by microorganisms.

4. The amine analysis method of claim 3, wherein the food is soy sauce.

5. The amine analysis method of claim 4, wherein the soy sauce is pretreated with acetonitrile (ACN) before derivatization with the fluorescence derivatization reagent.

6. The amine analysis method of claim 1, wherein the amine is a polyamine having a plurality of amine groups.

7. The amine analysis method of claim 6, wherein the polyamine is histamine.

8. The amine analysis method of claim 7, wherein a quantitative analysis of histamine is determined.

9. The amine analysis method of claim 7, wherein the compound represented by the general formula (1) is provided in a N,N-dimethylformamide (DMF) solution, and which has a shelf life of at least 40 days without degradation in performance.

10. The amine analysis method of claim 1, wherein the amine is a polyamine and the fluorescence derivatization reagent is a reagent that when dissolved in a solvent for more than 40 days the fluorescence derivatization reagent does not deteriorate in reactivity with the polyamine and is capable of fluorescently derivatizing a polymine.

11. The amine analysis method of claim 10, wherein the amine is tyramine.

12. The amine analysis method of claim 1, wherein after derivatization with the fluorescence derivatization reagent, 2 molecules of the compound represented by the general formula (1) are bound to one amine molecule.

13. The amine analysis method of claim 12, wherein an intensity of excimer fluorescence is measured after the binding of the molecules of the compound represented by the general formula (1) to the amine molecule.

14. The amine analysis method of claim 13, wherein the excimer fluorescence is measured by high performance liquid chromatography (HPLC) analysis.

15. The amine analysis method of claim 1, wherein R2 is an alkyl chain having from 1 to 4 carbon atoms.

16. The amine analysis method of claim 3, wherein R1 is an alkyl group having from 1 to 4 carbon atoms.

* * * * *